US009931272B2

(12) United States Patent
Sadkhin

(10) Patent No.: US 9,931,272 B2
(45) Date of Patent: Apr. 3, 2018

(54) METHOD FOR REDUCING A PERSON'S WEIGHT THROUGH HUNGER CONTROL

(76) Inventor: Gregory Sadkhin, Staten Island, NY (US)

( * ) Notice: Subject to any disclaimer, the term of this patent is extended or adjusted under 35 U.S.C. 154(b) by 663 days.

(21) Appl. No.: 13/112,701

(22) Filed: May 23, 2011

(65) Prior Publication Data

US 2011/0319966 A1 Dec. 29, 2011

Related U.S. Application Data

(60) Provisional application No. 61/333,286, filed on May 21, 2010.

(51) Int. Cl.
*A61N 1/18* (2006.01)
*A61H 39/00* (2006.01)

(52) U.S. Cl.
CPC ....... *A61H 39/00* (2013.01); *A61H 2230/805* (2013.01)

(58) Field of Classification Search
CPC ............ A61N 1/36085; A61N 1/36014; A61N 1/0541; A61N 1/36038; A61F 5/0026; A61H 39/00; A61H 39/002; A61H 2230/805
USPC .................. 607/58, 137; 600/378, 559, 548; 381/330
See application file for complete search history.

(56) References Cited

U.S. PATENT DOCUMENTS 5,366,483 A * 11/1994 Sadkhin .................. A61N 1/00 128/907
6,678,557 B1 * 1/2004 Tumey ..................... A61N 1/32 607/2
7,346,390 B1 * 3/2008 Tumey ..................... A61N 1/32 607/2
2006/0122675 A1 * 6/2006 Libbus ................. A61N 1/0551 607/116
2008/0288016 A1 * 11/2008 Amurthur .............. A61B 5/021 607/44

* cited by examiner

*Primary Examiner* — Michael Carey
(74) *Attorney, Agent, or Firm* — Daniel Basov, Esq.

(57) ABSTRACT

A method for reducing an individual's weight through hunger control is provided, wherein predetermined biologically active hunger control points and/or areas on the skin are stimulated utilizing removably attached point stimulation elements (PSEs) (e.g., spherules, etc.), in accordance with a predefined configurable cyclical treatment schedule. Maintenance procedures are also performed by the individual, after a predetermined amount of treatment cycles, to maintain weight reduction benefits gained during the treatments. Additional optional features of the inventive hunger control method include application of at least one of: a dietary plan, a vitamin and chronologically selected herb plan, behavioral modification, and an physical activity protocol.

53 Claims, 8 Drawing Sheets

200

FIG. 7 (Example)

*Schematic representation of multiple feedback model of chrono-synchronized hunger points. In this model, pacemakers (central and peripheral circadian clocks) drive rhythms in physiology and behavior.*

METHOD FOR REDUCING A PERSON'S WEIGHT THROUGH HUNGER CONTROL

CROSS REFERENCE TO RELATED APPLICATIONS

The present patent application claims priority from the commonly assigned U.S. provisional patent application 61/333,286 entitled "Method for Reducing a Person's Weight Through Hunger Control", filed May 21, 2010.

FIELD OF THE INVENTION

This invention relates to a method for reducing an individual's weight. More particularly, this invention relates to a method wherein biologically active hunger control points and/or areas on the skin are stimulated in accordance with a predefined configurable cyclical schedule to reduce the individual's food cravings, thereby resulting in weight loss.

BACKGROUND OF THE INVENTION

It is well established in the fields of acupuncture, reflexology, and applied kinesiology that the body has biologically active points which can be treated, for example, with needles or with the application of pressure, to relieve tension and to normalize the functions of internal organs and muscles. The fixed locations of these treatment points have been well documented for centuries.

Attempts have been made in the past to achieve weight loss in individuals through acupuncture treatments directed at their biologically active points. However, such approaches suffer from a number of significant disadvantages. First, because the vast majority of weight-loss related points are located in various areas on a person's head, utilizing acupuncture needles on those areas requires a great deal of skill and care, so as not to accidentally cause damage. Second, because acupuncture treatments must be performed by licensed and highly trained professionals, the length and, most importantly, frequency of treatments that a person can receive are a factor of that person's financial ability and schedule. Third, many people have a strong aversion to needles, and thus experience significant discomfort from acupuncture treatments. In addition, all previously known weight loss techniques involving interaction with biologically active points did not take into account the specific timing of treatments.

A novel advantageous approach, that addressed and overcame the disadvantages of all previously known weight loss methodologies based on biologically active points, was disclosed in the commonly assigned co-pending U.S. patent application Ser. No. 10/273,064 entitled "HUNGER-CONTROL WEIGHT REDUCTION METHOD", which is hereby incorporated by reference herein in its entirety (hereinafter, the "'064 Application"). The '064 Application disclosed a method for reducing weight through use of hunger control which was effected as follows: two metal spherules are attached at predetermined points in contact with skin surfaces behind the ears of an individual. The points proximal to each ear are at mirror symmetrical locations relative to a medial sagittal plane of the individual's skull. At intervals during every day of one or more ten-day cycles, the spherules are rolled in contact with the respective skin surface points at a predetermined level of pressure and at a predetermined speed for a predetermined number of rotations. The '064 Application further disclosed that the stimulation of specific biologically active points on an individual in accordance with a particular schedule sends signals to the individual's brain via the hypothalamus and thereby changes the way the brain and the hypothalamus regulate their body's systems responsible for controlling hunger. The individuals to whom this technique was applied have found it much easier to conform to a prescribed food plan, leading to significant long-term weight loss. Furthermore, in contrast to previously known weight loss methods, the hunger control method taught in the '064 Application does not require the use of drugs or permanent dietary restrictions.

While the method disclosed by the '064 Application is advantageously effective, there have been a number of significant improvements made thereto in connection with additional research and practical implementation of the '064 Application methodology.

Accordingly, an object of the present invention is to provide significant improvements in the '064 Application weight-loss method.

A further, more specific object of the present invention is to modify the '064 Application weight-loss method to make it easier to use.

Yet another specific object of the present invention is to provide additional supplemental program components to the inventive improved hunger control method to enable long-term maintenance of the method's beneficial results, and to significantly increase the effectiveness of the improved inventive method.

These and other objects of the present invention are represented by the drawings and the accompanying descriptions herein.

BRIEF DESCRIPTION OF THE DRAWINGS

In the drawings, wherein like reference characters denote corresponding or similar elements throughout the various figures.

SUMMARY OF THE INVENTION

Figure 1:
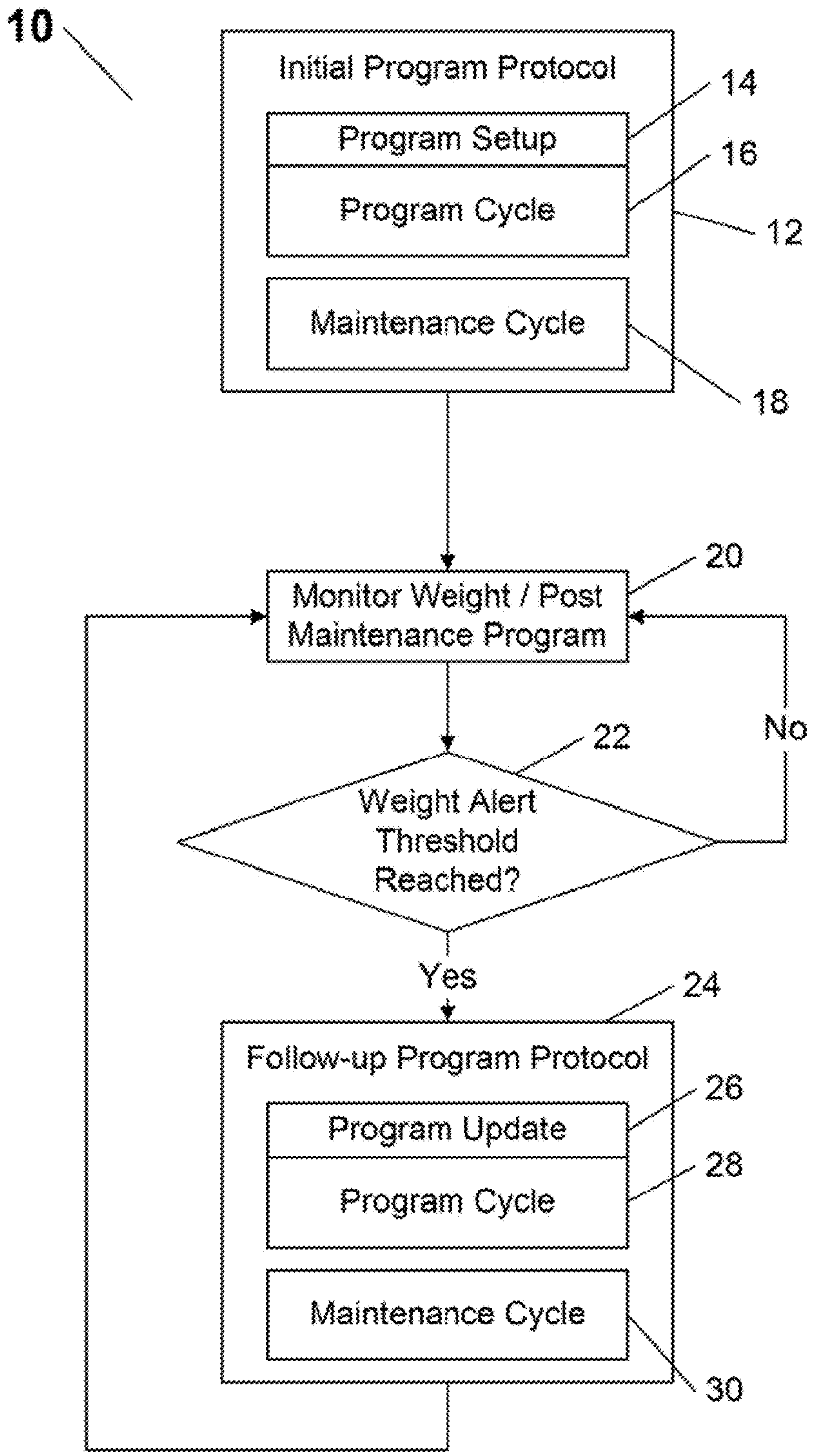
FIG. 1 is a flow process diagram showing the global program cycle of the novel method of weight reduction through hunger control of the present invention.

A method for reducing an individual's weight through hunger control is provided, wherein predetermined biologically active hunger control points and/or areas on the skin are stimulated utilizing removably attached point stimulation elements (PSEs) (e.g., spherules, etc.), in accordance with a predefined configurable cyclical treatment schedule. Maintenance procedures are also performed by the individual, after a predetermined amount of treatment cycles, to maintain weight reduction benefits gained during the treatments. Additional optional features of the inventive hunger control method include application of at least one of: a chrono-sensitive dietary plan, psychological reinforcement, a physical activity protocol, and a vitamin and seasonally-selected herb plan.

As described above, the '064 Application disclosed a method for reducing an individual's weight through use of hunger control which was effected by attaching two metal spherules at predetermined biologically active points in contact with skin surfaces behind the ears of an individual. The points proximal to each ear are selected to be at mirror symmetrical locations relative to a medial sagittal plane of the individual's skull. At intervals during every day of one or more ten-day cycles, the spherules are rolled in contact with the respective skin surface points at a predetermined level of pressure and at a predetermined speed, for a predetermined number of rotations. The '064 Application disclosed a methodology for locating and selecting the desirable biologically active points in several zones behind each ear of an individual as well as instructions for how the points, hereinafter referred to as "Sadkhin Points" were to be stimulated and also provided a first schedule for hourly stimulation during days of a program cycle in addition to a second schedule (in 10 day cycles) for selecting the days during which the first schedule is to be followed.

While the method disclosed by the '064 Application has proven to be advantageously effective, as evidenced by commercial success of its application by the inventor thereof, there have been a number of significant improvements thereto made by the inventor in connection with additional research and practical implementation of the '064 Application methodology.

In summary these improvements include, but are not limited to the following:

1) A long-term plan for implementing the inventive method in form of a global program cycle, with individual periodic program cycles interspaced with maintenance cycles;

2) A maintenance cycle methodology for advantageously maintaining the weight reduction achieved during a previous program cycle;

3) A protocol for varying implementation of the order and quantity of program sub-cycles during each program cycle to maximize the effectiveness thereof based on an individual's response to the treatments;

3) A set of optional components for use in connection with program cycle treatments, that greatly improve the effectiveness of the program cycles, that include, but are not limited to: Restrictive Feeding, Behavioral Modification, Physical Activity Protocol, and Continued and Seasonal Nutritional Supplements;

4) Expansion of effective Sadkhin Points stimulation protocols used during program cycles as well as of the devices used to effect the stimulation (now referred to as point stimulation elements (PSEs)); and 5) New techniques for optionally stimulating desirable biologically active points by manipulating zone areas surrounding the Sadkhin Points, rather than the points themselves.

In accordance with the above-described improvements, the method of the present invention achieves and exceeds all of its objectives to significantly increase the effectiveness of the '064 Application methodology, to enable long-term maintenance of the method's beneficial results, and to simplify its use and implementation.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

DETAILED DESCRIPTION OF PREFERRED EMBODIMENTS

Figure 8:
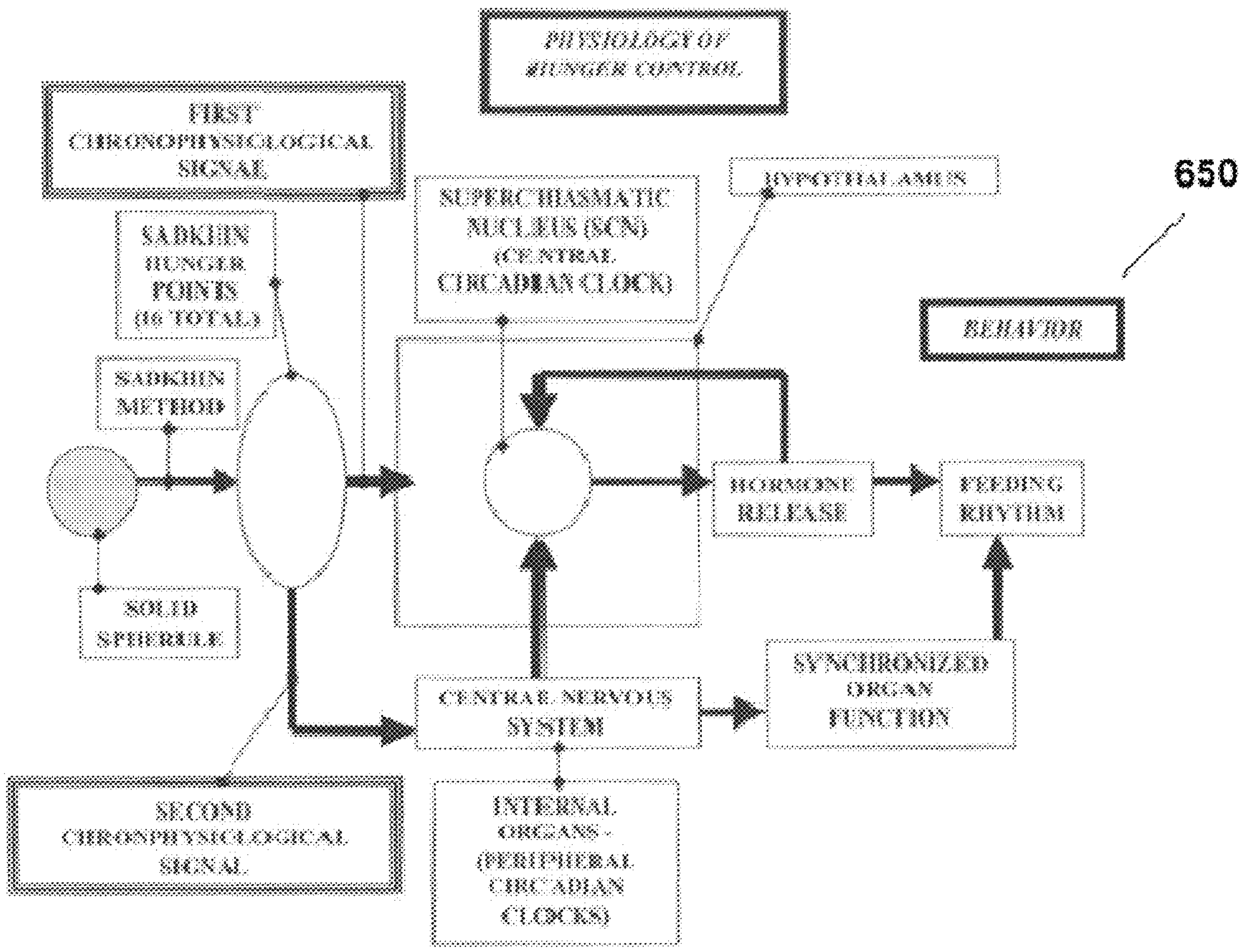
FIG. 8 is partially a block diagram, and partially a flow chart showing the chronosynchronizing physiological activity stimulated by the method of the present invention.

It should be noted at the outset, that the physiological mechanisms and principles on which the inventive hunger control method of the present invention is based, are described in greater detail in the above-incorporated commonly assigned co-pending U.S. Patent Application entitled "HUNGER-CONTROL WEIGHT REDUCTION METHOD", (the "'064 Application"). In summary, the '064 Application taught application of metal spherules to predetermined biologically active hunger control points (hereinafter referred to as "Sadkhin Points") on the skin surfaces behind the ears of an individual and rolled or rotated at those points in accordance with a predetermined cyclical schedule, to reduce that individual's desire to eat. This approach was based on the principle established by the inventor of the '064 Application and of the present invention, that stimulation of an individual's biologically active points in accordance with a specific protocol sends signals to the brain via the hypothalamus and thereby changes the way the brain and the hypothalamus regulate the body's systems responsible for controlling hunger. Referring to FIG. 8 hereto, a physiological activity 650 and the mechanism of stimulation thereof is described in greater detail in the above-incorporated '064 Application.

Prior to discussing the inventive method in greater detail, it would be helpful to provide an overview of the Sadkhin Points, the stimulation of which during the various phases of application of the inventive method, is a crucial component of the present invention.

Figure 5:
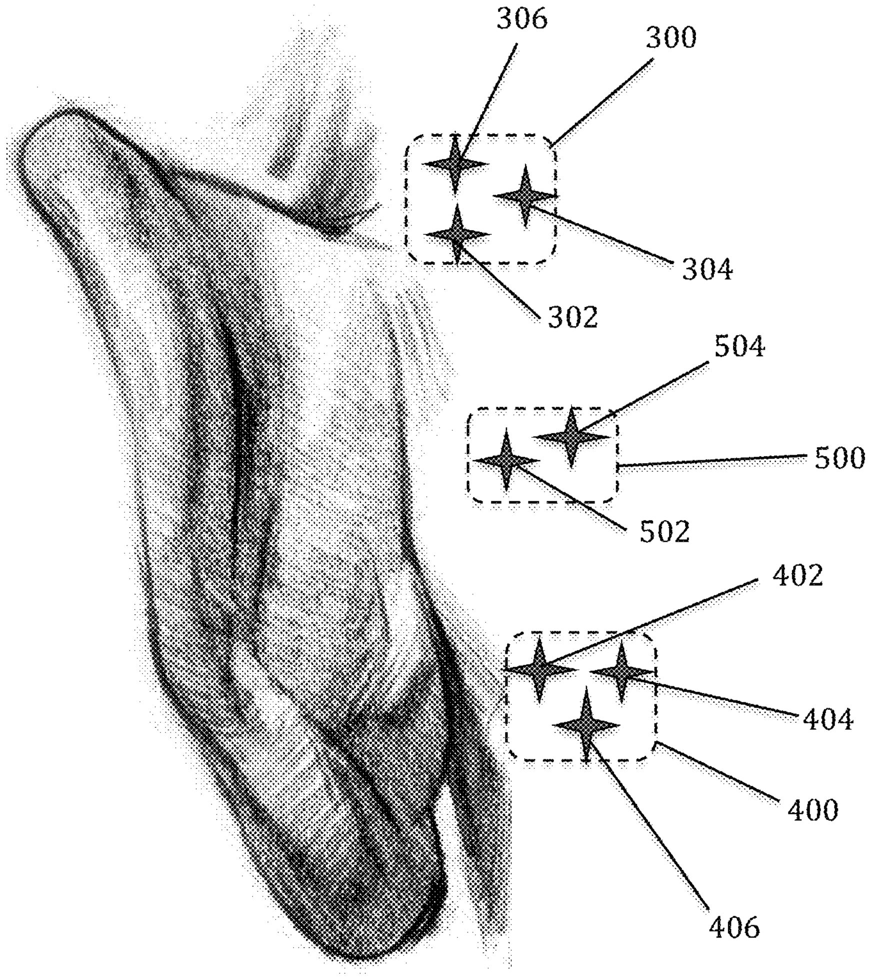
FIG. 5 is schematic partial rear view of a portion of person's head behind an ear, showing biologically active hunger control zones and points for use with the inventive weight reduction method of FIG. 1.

Referring now to FIG. 5, a set of Sadkhin Points 200 is shown in approximate locations in various areas behind each ear of an individual. Research and practical studies performed by the inventor have shown that the Sadkhin Points 200 have certain physiological properties which make them very different from other biologically active points. The Sadkhin Points 200 include 8 points located behind each ear of an individual (16 points total). The Points 200 are dispersed among three general zones 300, 400, and 500. Each of the zones 300, 400, and 500 has a physiological connection to a different group of an individual's internal organs. Zone 300 consists of three Points 302, 304, 306 that are associated with the stomach and liver. Zone 400 consists of three Points 402, 404, 408 that are associated with the small intestine and the large intestine. Zone 500 consists of two Points 502, 504, that are associated with the gallbladder and spleen. As disclosed in the '064 Application, stimulation of specific groups of these Points in accordance with predetermined chronological and cyclical protocols, results in advantageous control of the body's physiological mechanisms responsible for causing an individual to feel hungry.

While the '064 Application taught the stimulation of the specific Points 302 to 504, in accordance with the present invention, as an alternative to stimulating the specific points when required by the program cycle protocol, the entire Zones 300 to 500, may be generally stimulated. While this approach is less effective than direct stimulation of the specific Points, it may be far easier to implement by certain individuals (for example those that lack manual dexterity necessary for selecting and manipulating specific Sadkhin Points). Also, optionally, rather than actively stimulating the Points, the Points may be stimulated passively, for example, by attaching a removable stimulation element to one or more of the points.

Referring now to FIG. 1, a first embodiment of a global program cycle 10, that advantageously implements the weight reduction method of the present invention is shown. In summary, the inventive weight reduction method is preferably practiced in multiple program cycles, each with a number of program sub-cycles, with each program cycle being followed by a maintenance cycle and separated from the next program cycle by a period of time measured in months. The length of this period between a maintenance cycle and the next program cycle is dependent on the individual characteristics and weight of the person participating in the global program cycle 10 under the direction of a trained program administrator. Hereinafter for the sake of convenience, the person taking part in the global program cycle 10 will be referred to as a "participant", and the person and/or the entity directing and configuring the operation of the global program cycle 10 will be referred to as a "practitioner".

By undergoing periodic program cycles of the global program cycle 10, the participant can reduce their weight by a desired amount and maintain that reduction indefinitely, as long as the various requirements of the program cycles are adhered to, and the periodic program cycle are repeated as necessary (see FIG. 7, and the accompanying description below).

It should be noted that while a practitioner would typically be an individual, or a group of individuals, trained in the application of the global program cycle 10, a computer program (executed by a computer system) that is capable of, and configured for, emulating the decision-making capabilities of a human being, and that is supplied with necessary information about the global program cycle 10 and all necessary parameters and characteristics of a participant, can readily serve as a practitioner (either alone, under the direction of one or more persons, or, in a combination therewith), with respect to: (1) directing and guiding the participant through the global program cycle 10, and to (2) customizing the various parameters of the components of the global program cycle 10 to the needs and requirements of the participant, without departing from the spirit of the invention, as a matter of design choice or convenience.

Essentially, the global program cycle 10 begins with an initial program protocol 12, during which the participant interacts with the practitioner to configure and customize the various global program cycle components for the participant's needs and requirements, and most importantly during which the participant receives treatment in from of the program cycle and begins to reduce their weight. The initial program protocol 12 begins with program setup 14, during which, various parameters of the global program cycle 10 implementation are customized by the practitioner for the participant's needs and requirements. During program setup 14, the participant provides answers to a series of questions to establish the participants specific needs, requirements, and characteristics, (including, but not limited to: the desired target weight, current weight, current height, body fat percentage, body mass index, physical condition, psychological condition, medical conditions, allergies, dietary restrictions and/or requirements, and any other information about the participant's physical and/or mental conditions and well-being). In addition, during the program setup 14, the practitioner may acquire additional information about the participant by measurements or other forms of data acquisition and/or assessment, for example, by weighing the participant, measuring various body parts of the participant (waist, legs, neck, etc.), taking blood pressure measurements, taking body fat percentage measurements, measuring the body mass index, and so on. All of the information gathered at the program setup 14 may be utilized by the practitioner to make adjustments to the various parameters of the global program cycle 10 components, as well as for optional program cycle components (shown by way of example in FIG. 4, and described in greater detail below in connection therewith).

After the practitioner gathers the necessary information and configures the initial program protocol 12 at the program setup 14, a program cycle 16 is initiated. The key purpose of the program cycle 16 is to ensure that the participant achieves the desired weight reduction to a predetermined target weight, selected at the program setup 14. After the target weight is reached, or, if the participant wishes to exit the program cycle 16 before completing it properly, a maintenance cycle 18 is performed to stabilize the participant's lowered weight for as long as possible.

Thus, after completing the initial program protocol 12, the participant has achieved a desired level of weight reduction, and does not need to continue to perform the program cycle 16, unless the participant's weight increases by a particular predetermined amount, for example designated as a "weight alert threshold" which may be monitored as a step 20. In addition to monitoring their weight, the participant may also adhere to a post-maintenance program (for example, restriction on eating after 6 PM) that further locks-in the beneficial effects of the previous program protocol.

While some weight fluctuation over time is a fact of life, if the participant's weight increase exceeds the predetermined weight alert threshold value (for example as determined at step 22), the participant should return to the practitioner for a follow-up program protocol 22, which includes a program update step 26 (similar to the program setup 14, but aimed at updating the program protocol 24 for changes in participant's information), and also includes a program cycle 28 and subsequent maintenance cycle 30 (which are similar in principle to the program cycle 16 and maintenance cycle 18, but which may be modified therefrom based on the information gained at the program update step 26). The global program cycle 10 then continues at the step 20.

Figure 7:
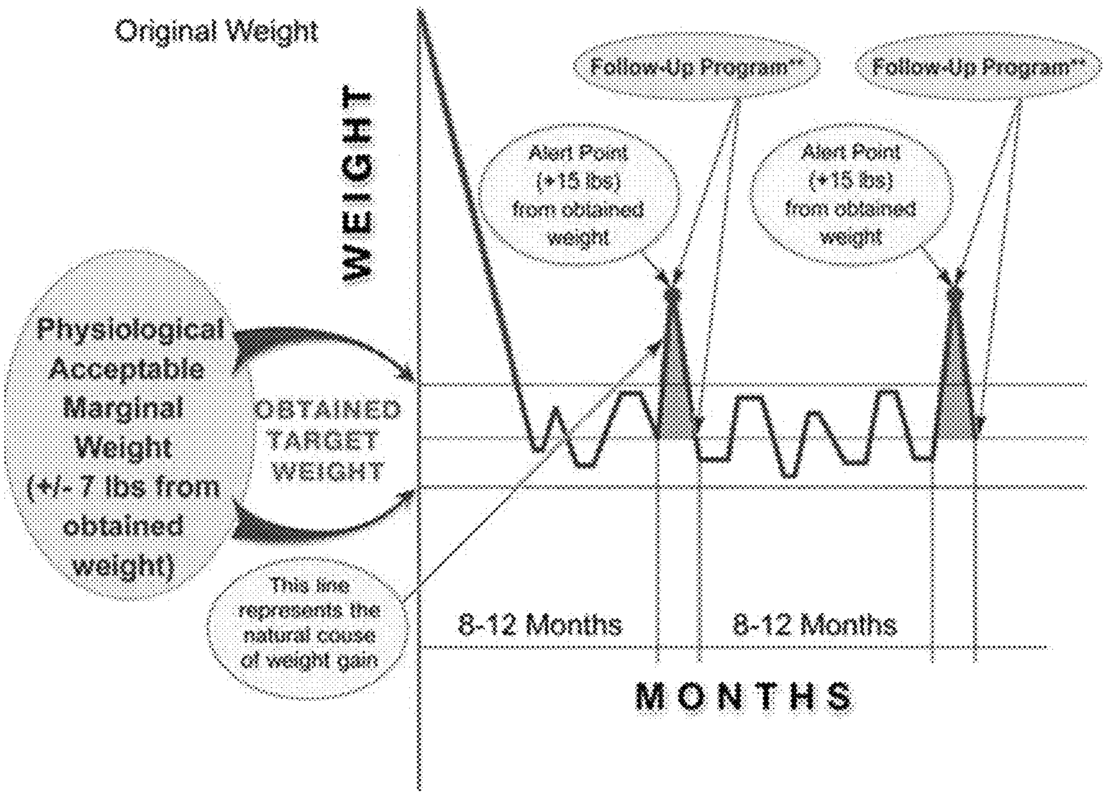
FIG. 7 is a graph showing exemplary implementation of the inventive weight reduction method of FIG. 1 over time.

Referring now to FIG. 7, an exemplary illustrative global program cycle 200 is shown, where the weight alert threshold is 15 pounds, and where periods between program protocols are 8-12 months.

Figure 2:
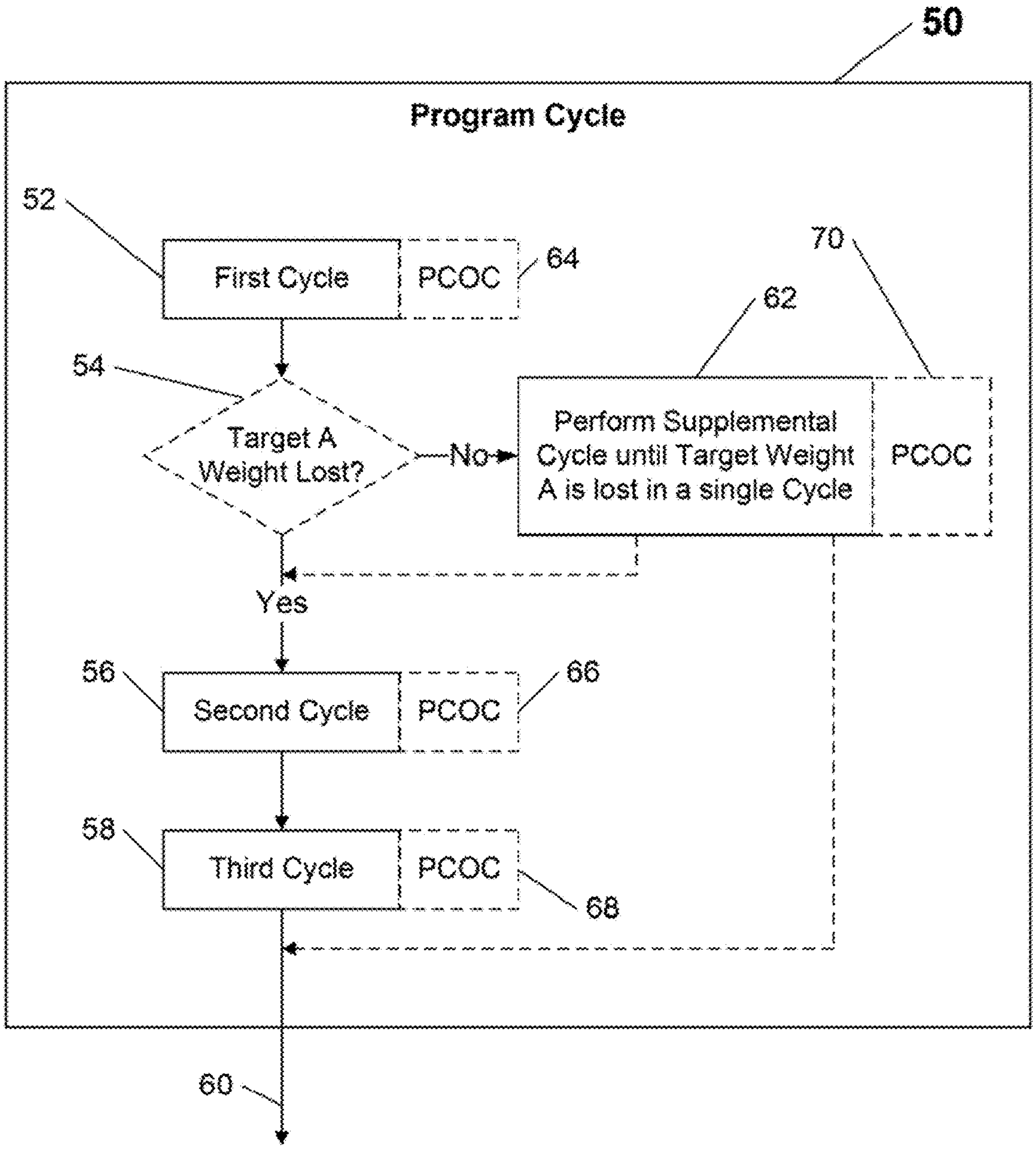
FIG. 2 is a flow process diagram showing an exemplary embodiment of a program cycle that's serves as a portion of the inventive global program cycle of FIG. 1.

Referring now to FIG. 2, an exemplary embodiment of the program cycles 16, 28, is shown as a program cycle 50. Prior to describing the cycle 50 components in greater detail, it should be noted that while a duration of approximately 10 days is preferable for each cycle component, this duration can be altered as a matter of design choice without departing from the spirit of the invention—for example the duration of any individual cycle can be between 7 and 14 days.

The program cycle 50 begins with a first cycle 52, which preferably is of an approximately 10 day duration. During cycle 52, a point stimulation element (hereinafter "PSE") (for example, a small spherule or similarly shaped object) is applied to each of the Points 302-306 (or optionally to the zone 300). The participant then moves the PSE in a predetermined manner to stimulate the Points. The number of movements of the PSEs during each stimulation may be selected as a matter of design choice, but should generally be between about 30 and 50 movements.

Various types of PSE repetitive movement patterns may be used in Point stimulation as a matter of design choice, but preferably, the PSEs are moved in small rotations—for example being rotated in small circles in a single direction (e.g., toward the participant's nose). In addition, the speed with which the PSEs are moved may be selected as a matter of design choice without departing from the spirit of the invention. Preferably, the PSEs are moved at a speed of between approximately one movement (e.g., rotation) every two seconds, and approximately two movements per second.

Preferably, small amounts of pressure should be applied on the PSE—just enough to make sure that the pressure feels the same behind each ear. The PSEs are then periodically manipulated in accordance with a daily program cycle protocol shown and described below in connection with FIG. 3).

Although steel is the preferred material for the PSEs used in the inventive hunger control methodology, other kinds of materials may be readily used without departing from the spirit of the invention as a matter of choice and/or convenience, including, but not limited to: metallic alloys, ceramics, polymers, resins, glass, stone, plastics, organic materials (for example: wood, plant seeds, bone, or other materials).

Optionally, each PSE may be removably attached to the skin area of the Points (appropriate to the then-current cycle) such that it can be manipulated as necessary while maintaining contact with the Points. For this purpose, any form of removable attachment techniques designed for use with skin can be used, for example, medical tape, flexible material coated with medical adhesive, or the like. Optionally, the PSEs may be used for passive stimulation of the points, for example being left in contact with one or more Points during each cycle.

Figure 3:
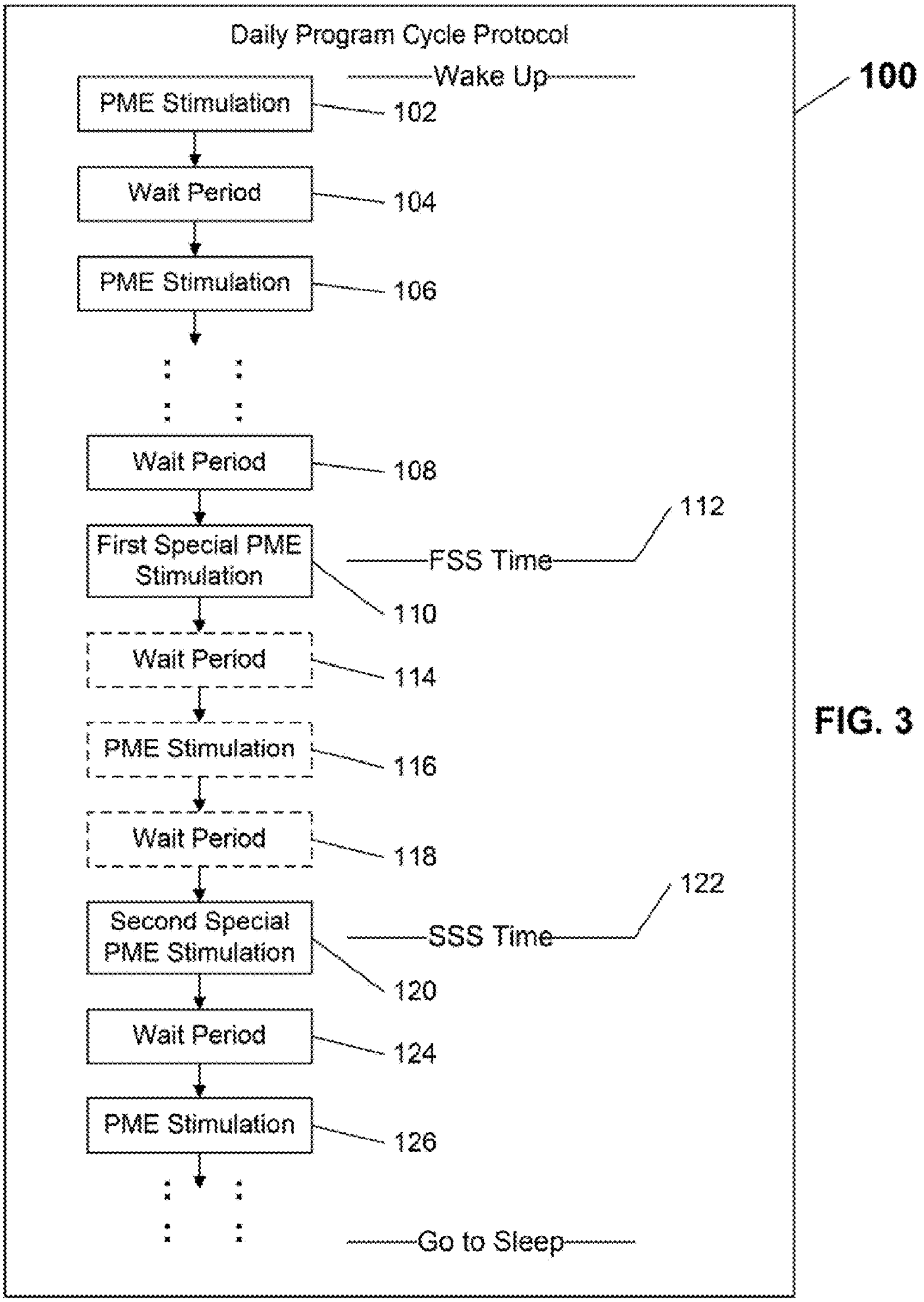
FIG. 3 is a flow process diagram showing an exemplary embodiment of a daily routine of the inventive program cycle of FIG. 2.

After completion of the first cycle 52, at an optional step 54, the practitioner determines if the participant has lost a predetermined amount of target weight A. This value is selected individually for each participant at the program setup 14 (FIG. 1) but is typically approximately 8-10 pounds. If the target weight A is lost, a second cycle 56 is initiated, which is similar to the cycle 52, except that the PSEs are used to stimulate Points 402-406 and include a variation in the daily program cycle protocol 100 (FIG. 3). Optionally, this step 54 may be bypassed and the program cycle 50 may then proceed from cycle 52 to cycle 56.

Following the second cycle 56, a third cycle 58 is initiated, which is similar to the cycle 52, except that the PSEs are used to stimulate Points 502 and 504 and include a variation in the daily program cycle protocol 100 (FIG. 3). At a step 60, the program cycle 50 is over and the participant may proceed to the maintenance cycle 18 (FIG. 1).

If at the optional step 54, the practitioner determines that the target weight A was not lost, at a step 62, the practitioner may institute one or more supplemental cycles until the target weight A is lost during one cycle, or until the practitioner is otherwise satisfied with the participant's progress. Preferably, the supplemental cycle consists of alternating performance of the first cycle 52, and the third cycle 58. Optionally, a different supplemental cycle protocol may be utilized.

Figure 4:
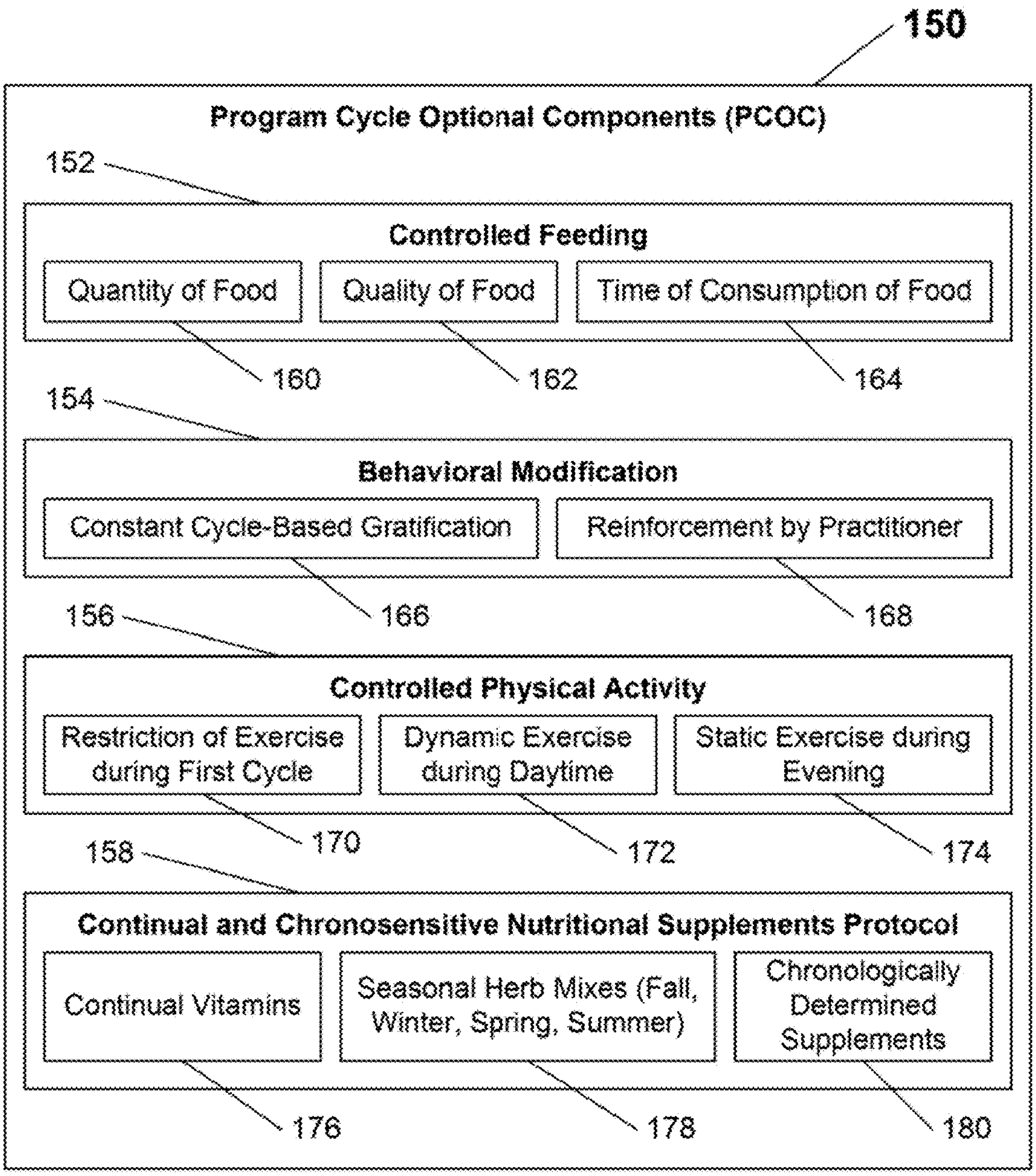
FIG. 4 is a schematic diagram showing exemplary embodiments of program cycle optional components for use in connection with the various portions of the global program cycle of FIG. 1.

In accordance with the present invention, the effectiveness of the global program cycle 10 (and of the individual program cycles) may be greatly increased with the use of program cycle optional components (PCOCs), shown in FIG. 4, and indicated as PCOCs 64-70 in FIG. 2. These PCOCs may vary between the cycles 52, 56 and 58, or may be similar or identical at each cycle, as a matter of choice by the practitioner. By way of example, the PCOCs 150 of FIG. 3 may include, but are not limited to:

- Controlled Feeding 150, which includes the elements of quantity of food 160, quality of food 162, and time of consumption of food 164. Quantity of food 160 relates to the sizes of the portions consumed by the participant. Quality of food 162 relates to the type of food consumed and beneficial and harmful characteristics thereof, such as meat, dairy, carbohydrates, fat content, etc. Time of consumption of food 164 relates to the times during the day at which the participant consumes the food. Various types of dietary restrictions can be implemented as restrictive feeding 150, as a matter of choice by the practitioner, for example depending on the particular characteristics and requirements of the participant;
- Behavioral Modification, which includes the elements of Constant Cycle-Based Gratification 166 and Reinforcement by Practitioner 168. Constant Cycle-Based Gratification 166 relates to the fact that the participant receives instant gratification at the end of each program cycle in form of weight reduction. Reinforcement by Practitioner 168 relates to the positive reinforcement of the participant's progress by the practitioner, and to verbal reinforcement by the practitioner of the principles of the inventive method to the participant at each opportunity;
- Controlled Physical Activity 156, which includes the elements of Restriction of Exercise during First Cycle 170, Dynamic Exercise during Daytime 172, and Static Exercise during Evening 174. Restriction of Exercise during First Cycle 170 relates to a restriction on exercise during a first cycle of any program cycle (for example first cycle 52 of program cycle 50 (FIG. 2)) while the participant's body is adjusting to the inventive method. Dynamic Exercise during Daytime 172, and Static Exercise during Evening 174 relate to the type of exercise which the participant may be encouraged to engage in at different times of day; and
- Continued and Seasonal Nutritional Supplements Protocol 158, which includes the elements of Continual Vitamins 176, Seasonal Herb Mixes (Fall, Winter, Spring, Summer) 178), and Chronologically Determined Supplements 180. The Continual Vitamins 176 relate to various vitamin supplements that may be recommended to the participant by the practitioner. Seasonal Herb Mixes 178 relate to mixtures of beneficial herbs (for example based on well-known naturopathic qualities, but that are selected based on the season they are taken, e.g., Fall, Winter, Spring, and Summer. Chronologically Determined Supplements 180 relate to different herbal supplements (for example, in form of teas) that may be recommended to the participant for consumption in morning for one type of supplement and in the evening for another type of supplement.

Referring now to FIG. 3, the exemplary daily program cycle protocol 100 is shown. In accordance with the present invention, the PSE stimulation times 102, 106, 116, and 126 (i.e., the times of day at which the PSEs are used to stimulate the appropriate Points), the wait periods 104, 108, 114, 118, and 124, and, most importantly, the first special PSE stimulation ("FSS") 110 and the second special PSE stimulation ("SSS") 120, along with the corresponding FSS time 112 (i.e., the time at which the FSS 110 is performed), and SSS time 122 (i.e., the time at which the SSS 120 is performed) are selected and determined in accordance with a current program cycle, i.e. depending on whether the current program cycle is 52, 56 or 58. The protocol 100 elements 102 to 126 may be selected as a matter of design choice, or the values shown and described in the '064 Application may be readily utilized.

Preferably, the wait periods 104, 108, 114, 118, and 124 are between approximately 1 to approximately 3 hours, while the FSS time 112 and SSS time 122 are preferably approximately 3 PM and 7 PM for cycle 52, approximately 4 PM and 7 PM for cycle 56, and approximately 2 PM and 7 PM for cycle 58. Certainly, other durations for wait periods 104, 108, 114, 118, and 124, and other FSS time 112 and SSS time 122 may be selected as a matter of design choice without departing from the spirit of the invention. It should also be noted that variations in the FSS time 112 and SSS time 122 of less than 1 hour are contemplated by the present invention. It should also be noted that in practical application of the method of this invention, superior results have been achieved with most participants by setting each of the wait periods 104, 108, 114, 118, and 124 to approximately 2 hours.

Figure 6:
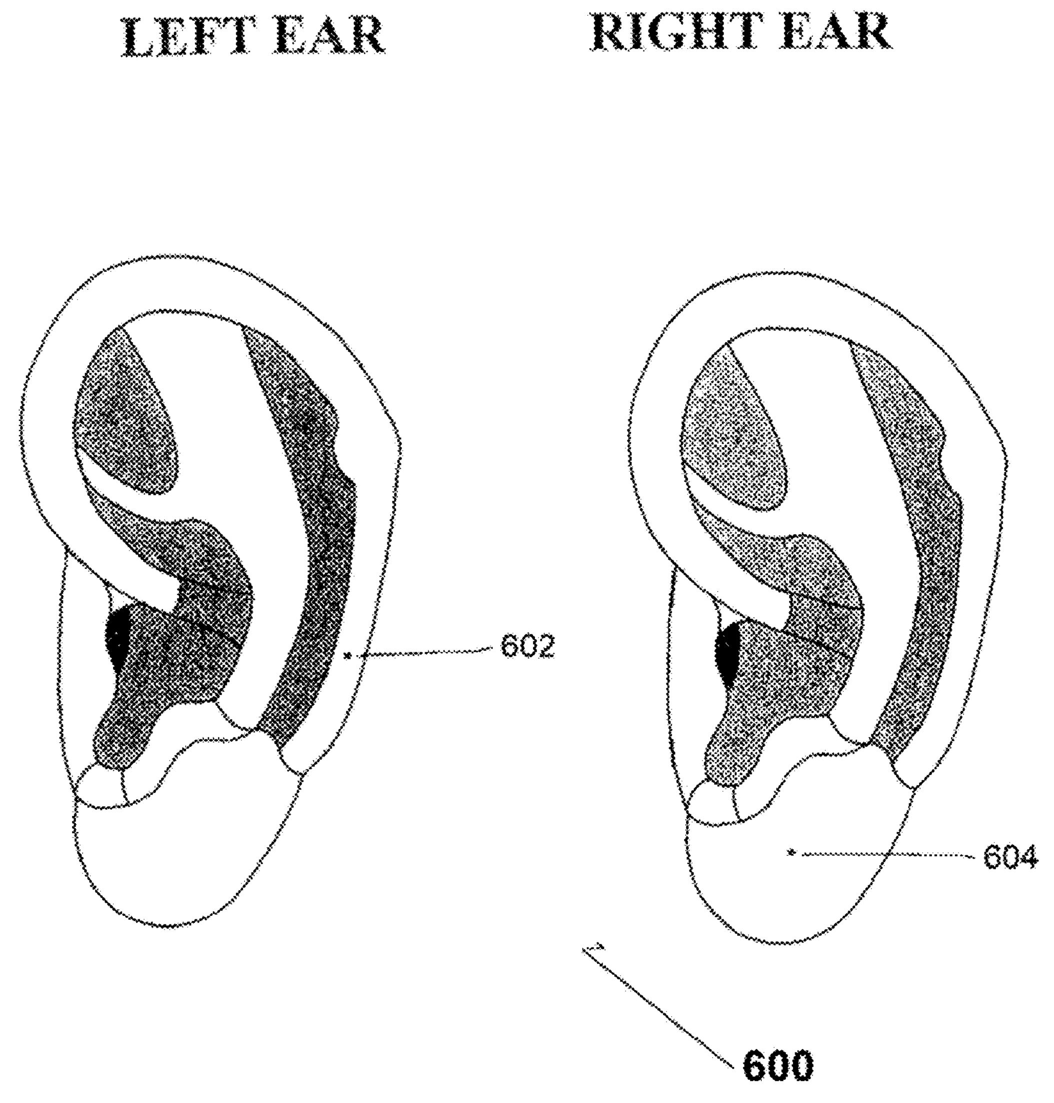
FIG. 6 is schematic view of a person's ears, showing biologically active points for use with the maintenance cycle program components of the inventive weight reduction method of FIG. 1.

As previously noted, the maintenance cycle 18 of FIG. 1 is an important element of the global program cycle 10. Referring now to FIG. 6, during the maintenance cycles 18, 30 the participant is provided with smaller version of the PSEs called maintenance elements (MEs) and applies them at a maintenance zone 600—each ME being applied to at approximately positioned maintenance points 602 and 604 on the left and right ears, respectively. Preferably, the maintenance point 602 is located at a lower portion of the outer helix of the left ear positioned between the middle portion of the helix and the earlobe, while the maintenance point 604 is located generally at the center of the outer earlobe of the right ear.

These MEs do not need to be manipulated—just left attached during the maintenance cycles 18, 30. Preferably, if the optional PCOC Restrictive Feeding 150 is utilized, the participant is instructed to eat only between specific hours, for example, between the hours of approximately 12 PM and 6 PM, plus or minus one hour for a participant with a normal day/night schedule.

As previously discussed in connection with FIG. 1, for maximum results, the participant should adhere to the global program cycle 10 on a continual basis.

Finally, while the inventive method is described above with reference to Sadkhin Points proximal to both ears being stimulated, it should be noted, that as a matter of design choice, only the Points proximal to a single ear may be stimulated during one or more particular cycles.

Thus, while there have been shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

I claim:

1. A method for reducing an individual's weight through hunger control, comprising the steps of:

(a) on each day during a first cycle of a first predetermined amount of days, applying a removable manual point stimulation element to at least one first biologically active area located proximal to and behind at least one ear of the individual, in accordance with a first stimulation protocol;

(b) on each day during a second cycle of a second predetermined amount of days, applying a removable manual point stimulation element to at least one second biologically active area located proximal to and behind the at least one ear of the individual, in accordance with a second stimulation protocol; and (c) on each day during a third cycle of a third predetermined amount of days, applying a removable manual point stimulation element to at least one third biologically active area located proximal to and behind the at least one ear of the individual, in accordance with a third stimulation protocol.

2. The method of claim 1, wherein said at least one first biologically active area comprises a first plurality of biologically active points on the skin surface of the individual, positioned proximal, to and behind an upper portion of each ear of the individual at mirror symmetrical locations relative to a medial sagittal plane of the individual's skull.

3. The method of claim 1, wherein said at least one second biologically active area comprises a second plurality of biologically active points on the skin surface of the individual, positioned proximal, to and behind a lower portion of each ear of the individual at mirror symmetrical locations relative to a medial sagittal plane of the individual's skull.

4. The method of claim 1, wherein said at least one third biologically active area comprises a third plurality of biologically active points on the skin surface of the individual, positioned proximal, to and behind a middle portion of each ear of the individual at mirror symmetrical locations relative to a media sagittal plane of the individual's skull.

5. The method of claim 2, wherein said first plurality of biologically active points comprises three points.

6. The method of claim 3, wherein said second plurality of biologically active points comprises three points.

7. The method of claim 4, wherein said third plurality of biologically active points comprises two points.

8. The method of claim 2, wherein said first stimulation protocol comprises the steps of:

(d) placing two point stimulation elements in skin contact with said first plurality of biologically active points, such that each of said two point stimulation elements is located behind a respective ear of the individual; and (e) at first predetermined intervals, moving said point stimulation elements while maintaining skin contact with said first plurality of biologically active points at a first predetermined level of pressure and at a first predetermined speed, for a first predetermined number of repetitions.

9. The method of claim 3, wherein said second stimulation protocol comprises the steps of:

(f) placing said two point stimulation elements in skin contact with said second plurality of biologically active points, such that each of said two point stimulation elements is located behind a respective ear of the individual; and (g) at second predetermined intervals, moving said point stimulation elements while maintaining skin contact with said second plurality of biologically active points at a second predetermined level of pressure and at a second predetermined speed, for a second predetermined number of repetitions.

10. The method of claim 4, wherein said third stimulation protocol comprises the steps of:

(h) placing said two point stimulation elements in skin contact with said third plurality of biologically active points, such that each of said two point stimulation elements is located behind a respective ear of the individual; and (i) at second predetermined intervals, moving said point stimulation elements while maintaining skin contact with said third plurality of biologically active points at a third predetermined level of pressure and at a third predetermined speed, for a third predetermined number of repetitions.

11. The method of claim 8, wherein each of said two point stimulation elements is a spherule composed of at least one of the following groups of materials: metallic alloys, ceramics, polymer, resins, glass, stone, plastics, and organic materials.

12. The method of claim 8, wherein said step (d) further comprises the step of:

(j) removably attaching each of said two point stimulation elements in skin contact with said first plurality of biologically active points to maintain said contact therewith for the duration of at least a portion of said first cycle.

13. The method of claim 9, wherein said step (f) further comprises the step of:

(k) removably attaching each of said two point stimulation elements in skin contact with said second plurality of biologically active points to maintain said contact therewith for the duration of at least a portion of said second cycle.

14. The method of claim 10, wherein said step (h) further comprises the step of:

(l) removably attaching each of said two point stimulation elements in skin contact with said third plurality of biologically active points to maintain said contact therewith for the duration of at least a portion of said third cycle.

15. The method of claim 8, wherein said first predetermined level of pressure is a level of pressure sufficient to cause a1 least a modicum of discomfort to the individual.

16. The method of claim 9, wherein said second predetermined level of pressure is a level of pressure sufficient to cause at least a modicum of discomfort to the individual.

17. The method of claim 10 wherein said third predetermined level of pressure is a level of pressure sufficient to cause at least a modicum of discomfort to the individual.

18. The method of claim 8, wherein said first predetermined level of speed is between about one point stimulation element movement every two seconds to two point stimulation elements movements per second.

19. The method of claim 9, wherein said second predetermined level of speed is between about one point stimulation element movement every two seconds to two point stimulation elements movements per second.

20. The method of claim 10, wherein said third predetermined level of speed is between about one point stimulation element movement every two seconds to two point stimulation elements movements per second.

21. The method of claim 8, wherein said first predetermined number of repetitions is between about 30 to about 50 repetitions.

22. The method of claim 9, wherein said second predetermined number of repetitions is between about 30 to about 50 repetitions.

23. The method of claim 10, wherein said third predetermined number 20 of repetitions is between about 30 to about 50 repetitions.

24. The method of claim 8, wherein said first predetermined intervals are between about one hour and three hours each.

25. The method of claim 9, wherein said second predetermined intervals are between about one hour and three hours each.

26. The method of claim 10, wherein said third predetermined intervals are between about one hour and three hours each.

27. The method of claim 8, further comprising the step of:

(m) at a first predetermined time of day, and again, at a second predetermined time of day, moving said point stimulation elements while maintaining skin contact with said first plurality of biologically active points at said first predetermined level of pressure and at said first predetermined speed, for said first predetermined number of repetitions.

28. The method of claim 27, wherein said first predetermined time of day is approximately 3 P.M., and wherein said second predetermined time of day is approximately 7 P.M.

29. The method of claim 9, further comprising the step of:

(n) at a third predetermined time of day, and again, at a fourth predetermined time of day, moving said point stimulation elements while maintaining skin contact with said second plurality of biologically active points at said second predetermined level of pressure and at said second predetermined speed, for said second predetermined number of repetitions.

30. The method of claim 29, wherein said third predetermined time of day is approximately 4 P.M., and wherein said fourth predetermined time of day is approximately 7 P.M.

31. The method of claim 10, further comprising the step of:

(o) at a fifth predetermined time of day, and again, at a sixth predetermined time of day, moving said point stimulation elements while maintaining skin contact with said third plurality of biologically active points at said third predetermined level of pressure and at said third predetermined speed, for said third predetermined number of repetitions.

32. The method of claim 29, wherein said fifth predetermined time of day is approximately 2 P.M., and wherein said sixth predetermined time of day is approximately 7 P.M.

33. The method of claim 1, further comprising the steps of:

(p) prior to said step (a) determining a desired first target weight loss amount;

(q) when said first target weight loss amount is lost by the individual after said step (a), proceeding to said step (b); and (r) when said first target weight loss amount is not lost by the individual after said step (a); prior to proceeding to said step (b), performing a supplemental biologically active point stimulation process until said first target weight loss amount is lost by the individual.

34. The method of claim 33, wherein said supplemental biologically active point stimulation process comprises the step of:

(s) selectively performing said steps (a) and (c) in an alternating order.

35. The method of claim 33, further comprising the steps of:

(t) prior to said step (p), collecting personal information from the individual representative of at least a portion of the following group of information items specific to the individual: current weight, current height, body fat percentage, body mass index, target weight desired by the individual, medical conditions, dietary restrictions and requirements, physical condition, psychological condition, allergies, measurements of circumference of body parts of the individuals comprising measurements of circumference of legs, arms, torso, chest and neck, blood pressure, and cholesterol level; and (u) at said step (p) determining said first target weight loss amount based at least in part on said personal information gathered at said step (t).

36. The method of claim 35, further comprising the step of:

(u2) based on said personal information gathered at said step (t), implementing at least one supplemental weight procedure for the individual during performance of at least a one of said steps (a), (b), and (c).

37. The method of claim 36, wherein said at least one supplemental weight loss procedure comprises at least one procedure selected from the group comprising: controlled feeding, behavioral modification, controlled physical activity, and consumption of nutritional supplements in accordance with a nutritional supplement protocol.

38. The method of claim 37, wherein said controlled feeding comprises at least one of the following steps:

(v) controlling a quantity of food consumed by the individual during performance of said steps (a), (b), and (c);

(w) controlling a type of food consumed by the individual during performance of said steps (a), (b), and (c); and (x) controlling times of day during which different types of food are consumed by the individual during performance of said steps (a), (b), and (c).

39. The method of claim 37, wherein said behavioral modification comprising the step of:

(y) providing positive reinforcement to the individual based on weight lost by the individual after performance at least one of steps (a), (b), and (c).

40. The method of claim 37, wherein said controlled physical activity comprises at least one of the following steps:

(z) restricting exercise by the individual during said step (a);

(aa) engaging by the individual, in dynamic exercises during daytime hours; and (bb) engaging, by the individual, in static exercises during evening hours.

41. The method of claim 37, wherein said nutritional supplement protocol comprises at least one of the following steps:

(cc) consuming, by the individual, of vitamins selected based on at least a portion of said personal information;

(dd) utilizing, by the individual, seasonal herb mixes selected based on the season of the year at the time of performance of said steps (a), (b), and (c); and (ee) consuming, by the individual, of chronologically determined supplements selected based on the time of day at the time of consumption.

42. The method of claim 1, further comprising the step of:

(ff) after said step (c), performing a weight maintenance procedure to substantially maintain, by the individual, the weight lost during said steps (a), (b), and (c) for a predetermined period of time.

43. The method of claim 42, wherein said weight maintenance procedure comprises the steps of:

(gg) maintaining a first maintenance element in skin contact with a first biologically active maintenance point for at least a portion of said predetermined period of time; and (hh) maintaining a second maintenance element in skin contact with a second biologically active maintenance point for at least a portion of said predetermined period of time.

44. The method of claim 43, wherein said weight maintenance procedure further comprises the step of:

(ii) restricting food intake of the individual during the predetermined period of time so that the individual only consumes food during a predetermined portion of a day.

45. The method of claim 43, wherein said first biologically active maintenance point is positioned at a lower portion of the outer helix of the left ear of the individual, between the middle portion of the helix and the earlobe.

46. The method of claim 43, wherein said second biologically active maintenance point is positioned generally at the center of the outer earlobe of the right ear of the individual.

47. The method of claim 1, further comprising the steps of:

(jj) after said step (c), determining a weight alert threshold for the individual;

(kk) monitoring the individual's weight to determine whether the individual has reached said weight alert threshold; and (ll) when said weight alert threshold has been reached, returning to said step (a).

48. The method of claim 47, further comprising the steps of:

(mm) after said step (ll) and prior to returning to said step (a) collecting personal information from the individual representative of at least a portion of the following group of information items specific to the individual: current weight, current height, body fat percentage, body mass index, target weight desired by the individual, medical conditions, dietary restrictions and requirements, physical condition, psychological condition, allergies, measurements of circumference of body parts of the individuals comprising measurements of circumference of legs, arms, torso, chest and neck, blood pressure, and cholesterol level; and (nn) selectively revising at least one of said first, second and/or third stimulation protocols, in response to said collected personal information.

49. The method of claim 1, wherein said first predetermined amount of days is selected from between approximately seven and fourteen days.

50. The method of claim 1, wherein said second predetermined amount of days is selected from between approximately seven and fourteen days.

51. The method of claim 1, wherein said third predetermined amount of days is selected from between approximately seven and fourteen days.

52. A method for reducing an individual's weight by a predetermined target weight amount through hunger control, comprising the steps of:

(a) on each day during a first cycle of a first predetermined amount of days, applying a removable manual point stimulation element to at least one first biologically active area located proximal to and behind each ear of the individual, in accordance with a first stimulation protocol;

(b) selecting at least on different biologically active area and at least one different stimulation protocol; and (c) selectively repeating said steps (a) and (b) until said predetermined target weight amount is lost, at each repetition of said step (a) (selectively utilizing one of said at least one first biologically active area and said at least one different biologically active area, and selectively utilizing one of said first stimulation protocol and said different stimulation protocol.

53. A system for reducing an individual's weight by a predetermined target weight amount through hunger control, comprising (a) a first at least two point stimulation elements in skin contact with a first plurality of biologically active points, such that each of said two point stimulation elements is located behind a respective ear of the individual; and at first predetermined intervals, moving said first two point stimulation elements while maintaining skin contact with said first plurality of biologically active points at a first predetermined level of pressure and at a first predetermined speed, for a first predetermined number of repetitions;

(b) a second at least two point stimulation elements in skin contact with a second plurality of biologically active points, such that each of said two point stimulation elements is located behind a respective ear of the individual, and at second predetermined intervals, moving said second point stimulation elements while maintaining skin contact with said second plurality of biologically active points at a second predetermined level of pressure and at a second predetermined speed, for a second predetermined number of repetitions;

(c) wherein said first and second at least two point simulation elements are repeatedly moved at the corresponding first and second predetermined stimulation protocol for each of said at least two point simulation elements.

* * * * *